(12) United States Patent
Niederberger et al.

(10) Patent No.: US 7,655,029 B2
(45) Date of Patent: Feb. 2, 2010

(54) BONE PLATE

(75) Inventors: Alfred Niederberger, Grenchen (CH);
Eric Hattler, Solothurn (CH)

(73) Assignee: Synthes USA, LLC, West Chester, PA (US)

( * ) Notice: Subject to any disclaimer, the term of this patent is extended or adjusted under 35 U.S.C. 154(b) by 1068 days.

(21) Appl. No.: 10/721,895

(22) Filed: Nov. 26, 2003

(65) Prior Publication Data
US 2004/0167522 A1    Aug. 26, 2004

Related U.S. Application Data

(63) Continuation of application No. PCT/CH01/00327, filed on May 28, 2001.

(51) Int. Cl.
*A61B 17/80* (2006.01)
(52) U.S. Cl. .................................................. 606/280
(58) Field of Classification Search ............. 606/69–71, 606/61, 280–299
See application file for complete search history.

(56) References Cited

U.S. PATENT DOCUMENTS

| | | | |
|---|---|---|---|
| 3,552,389 A | 1/1971 | Allgower et al. | |
| 3,596,656 A | 8/1971 | Kaute | |
| 3,630,261 A | 12/1971 | Gley | |
| 3,668,972 A | 6/1972 | Allgower et al. | |
| 3,716,050 A | 2/1973 | Johnston | |
| 3,779,240 A * | 12/1973 | Kondo | 606/69 |
| RE28,841 E | 6/1976 | Allgower et al. | |
| 4,219,015 A | 8/1980 | Steinemann | |
| 4,338,926 A | 7/1982 | Kummer et al. | |
| 4,408,601 A | 10/1983 | Wenk | |
| RE31,628 E | 7/1984 | Allgower et al. | |
| 4,493,317 A | 1/1985 | Klaue | |
| 4,513,744 A | 4/1985 | Klaue | |
| 4,565,193 A | 1/1986 | Streli | |
| 4,838,252 A | 6/1989 | Klau | |
| 4,867,144 A | 9/1989 | Karas et al. | |
| 4,927,421 A | 5/1990 | Goble et al. | |
| 4,957,497 A | 9/1990 | Hoogland et al. | |
| 4,988,350 A | 1/1991 | Herzberg | |
| 5,002,544 A | 3/1991 | Klaue et al. | |
| 5,006,120 A | 4/1991 | Carter | |
| 5,041,114 A | 8/1991 | Chapman et al. | |
| 5,085,660 A | 2/1992 | Lin | |
| 5,108,399 A | 4/1992 | Eitenmuller et al. | |

(Continued)

FOREIGN PATENT DOCUMENTS

CH    611147    5/1979

(Continued)

*Primary Examiner*—Thomas C Barrett
*Assistant Examiner*—Michael J Araj
(74) *Attorney, Agent, or Firm*—Fay Kaplun & Marcin, LLP

(57) ABSTRACT

A bone plate for fixation of proximal humerus fractures comprises an elongated shaft portion having a first width and a head portion connected to the shaft portion having a second width greater than the first width. The head portion and the shaft portion define a common longitudinal axis. At least one first screw hole may be located in the head portion, and at least one second screw hole may be located in the shaft portion. At least one of the first and second holes is configured to engage a head of a bone screw to form an angularly stable connection with the bone screw.

18 Claims, 4 Drawing Sheets

U.S. PATENT DOCUMENTS

| | | | |
|---|---|---|---|
| 5,129,901 A | 7/1992 | Decoste | |
| 5,151,103 A | 9/1992 | Tepic et al. | |
| 5,190,544 A | 3/1993 | Chapman et al. | |
| 5,197,966 A | 3/1993 | Sommerkamp | |
| 5,259,398 A | 11/1993 | Vrespa | |
| 5,269,784 A | 12/1993 | Mast | |
| 5,275,601 A | 1/1994 | Gogolewski et al. | |
| 5,304,180 A | 4/1994 | Slocum | |
| 5,324,290 A | 6/1994 | Zdeblick et al. | |
| 5,364,398 A | 11/1994 | Chapman et al. | |
| 5,364,399 A | 11/1994 | Lowery et al. | |
| 5,429,641 A | 7/1995 | Gotfried | |
| 5,487,741 A | 1/1996 | Maruyama et al. | |
| 5,514,138 A | 5/1996 | McCarthy | |
| 5,534,027 A | 7/1996 | Hodorek | |
| 5,591,168 A | 1/1997 | Judet et al. | |
| 5,601,553 A | 2/1997 | Trebing et al. | |
| 5,607,428 A | 3/1997 | Lin | |
| 5,674,222 A | 10/1997 | Berger et al. | |
| 5,683,460 A | 11/1997 | Persoons | |
| 5,702,399 A | 12/1997 | Kilpela et al. | |
| 5,709,686 A | 1/1998 | Talos et al. | |
| 5,741,258 A | 4/1998 | Klaue et al. | |
| 5,749,872 A | 5/1998 | Kyle et al. | |
| 5,772,662 A | 6/1998 | Chapman et al. | |
| 5,810,823 A | 9/1998 | Klaue et al. | |
| 5,863,201 A | 1/1999 | Lazzara et al. | |
| 5,938,664 A | 8/1999 | Winquist et al. | |
| 5,954,722 A | 9/1999 | Bono | |
| 5,968,047 A | 10/1999 | Reed | |
| 6,022,352 A | 2/2000 | Vandewalle | |
| 6,096,040 A * | 8/2000 | Esser | 606/280 |
| 6,129,730 A | 10/2000 | Bono et al. | |
| 6,183,475 B1 | 2/2001 | Lester et al. | |
| 6,206,881 B1 | 3/2001 | Frigg et al. | |
| 6,228,085 B1 | 5/2001 | Theken et al. | |
| 6,283,969 B1 | 9/2001 | Grusin | |
| 6,306,136 B1 | 10/2001 | Baccelli | |
| 6,322,562 B1 | 11/2001 | Wolter | |
| 6,364,882 B1 | 4/2002 | Orbay | |
| 6,440,135 B2 | 8/2002 | Orbay et al. | |
| 6,454,770 B1 | 9/2002 | Klaue | |
| 6,508,819 B1 | 1/2003 | Orbay | |
| 6,527,776 B1 | 3/2003 | Michelson | |
| 6,572,622 B1 * | 6/2003 | Schafer et al. | 606/69 |
| D479,331 S | 9/2003 | Pike et al. | |
| 6,623,486 B1 * | 9/2003 | Weaver et al. | 606/69 |
| 6,669,701 B2 | 12/2003 | Steiner et al. | |
| 6,712,820 B2 * | 3/2004 | Orbay | 606/69 |
| 6,719,759 B2 * | 4/2004 | Wagner et al. | 606/69 |
| 2002/0156474 A1 * | 10/2002 | Wack et al. | 606/69 |

FOREIGN PATENT DOCUMENTS

| | | |
|---|---|---|
| CN | 2102729 | 4/1992 |
| CN | 2169386 | 6/1994 |
| DE | 43 41 980 A1 | 6/1995 |
| DE | 43 43 117 A1 | 6/1995 |
| DE | 44 38 264 A1 | 3/1996 |
| DE | 93 21 544 U1 | 10/1999 |
| EP | 0 207 884 A2 | 1/1987 |
| EP | 1 468 655 A2 | 10/2004 |
| FR | 2233973 | 1/1975 |
| FR | 2405062 | 5/1979 |
| FR | 2405705 | 5/1979 |
| FR | 2405706 | 5/1979 |
| FR | 2496429 | 5/1979 |
| SU | 1279626 A1 | 12/1986 |
| WO | WO 97/09000 | 3/1997 |
| WO | WO 00/53110 | 9/2000 |
| WO | WO 00/53111 | 9/2000 |
| WO | WO 01/19267 | 3/2001 |

* cited by examiner

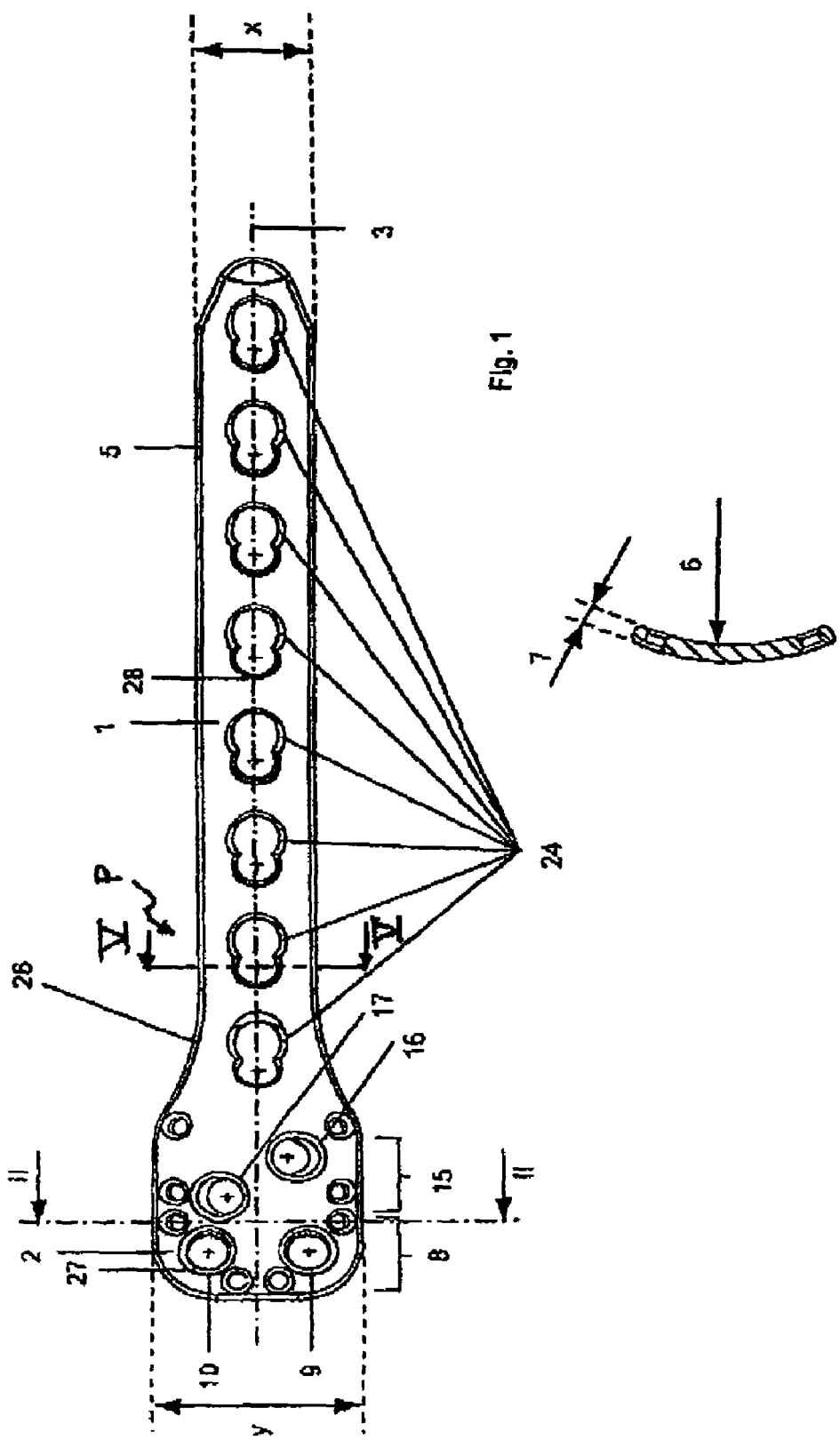

BONE PLATE

CROSS-REFERENCE TO RELATED APPLICATIONS

The present application is a continuation of the U.S. National Stage designation of copending International Patent Application No. PCT/CH01/00327, filed May 28, 2001, the entire content of which is expressly incorporated herein by reference thereto.

TECHNICAL FIELD OF THE INVENTION

The present invention relates generally to bone plates for fixation of long bones. More specifically, the present invention relates to bone plates for fixation of multiple-part and dislocated fractures of the long bones, such as those of the proximal humerus.

BACKGROUND OF THE INVENTION

In recent years, a common cause of fractures of the proximal humerus has been high-energy trauma. The occurrence of this type of fracture increases with age because the bone structure in the area of the proximal humerus degrades over time, such that only the edge zone of the bone in the region of the proximal humerus remains intact. In the event of a fall on an outstretched arm at advanced age, the bone commonly breaks in the area of the proximal humerus.

One type of bone plate known in the art includes a head section and an elongated shaft portion. The head portion includes two pairs of holes forming a generally T-shaped configuration on the head portion. One disadvantage of this type of bone plate is that the hole configuration of the head portion may inhibit inserting screws into the intact bone structure located at the edge zone of the proximal humerus. Moreover, the known bone plates may lack angularly stable options in the plate holes. When using such a bone plate, it may be pressed by bone screws against the bone, a process called compression osteosynthesis. In compression osteosynthesis, the forces which arise are transferred via friction between the implant or plate and the bone, with the bone bearing most of the load. Under dynamic conditions, the axial pressure applied on the bone screws may cause the bone screws to tear out of the bone, and may result in a loss of the stability of the plate-bone construct. In order to achieve angularly-stable repositioning, some implants from the prior art required blades. The prior art surgical technique of using blades, however, requires greater time expenditure and is complex to use. Therefore, there remains a need in the art for bone plates having angular stability between the bone plate and the screws, simple handling, and optimum anatomic matching to the bone with no impediment to the relevant anatomic structures of the bone.

SUMMARY OF THE INVENTION

The present invention is directed to a bone plate for fixation of bone fractures, for examples, fractures of the proximal humerus in which angularly stable osteosynthesis can be achieved. The bone plate may be used for both the left and also for the right humerus and may be optimally matched to the shape of a healthy proximal humerus. A first embodiment of the bone plate may include an elongated shaft portion having a first width and a head portion connected to the shaft portion having a second width greater than the first width. The head portion and the shaft portion may define a common longitudinal axis. At least one first screw hole may be located in the head portion, at least one second screw hole may be located in the shaft portion, and at least one of the first and second holes may be configured to engage a head of a bone screw to form an angularly stable connection with the bone screw.

In one preferred embodiment, at least one of the first and second holes may be at least partially threaded, and the thread may have a pitch of about 0.5 mm to about 1.1 mm. In another preferred embodiment, the thread may have a pitch of about 0.7 mm to about 0.9 mm. In yet another embodiment, the thread may be double threaded.

In an alternative embodiment, at least one of the first and second holes includes at least a partial peripheral groove for engaging a head of a bone screw. The peripheral groove may be substantially wedge shaped.

The bone plate according to the present invention may have a thickness ranging from about 1.7 mm to about 2.3 mm. In another embodiment, the bone plate may have a thickness ranging from about 1.9 mm to about 2.1 mm.

The head portion of the bone plate according to the present invention may be connected to the shaft portion at a transition area having a third width that increases from the first width to the second width. In one preferred embodiment the third width widens exponentially.

The bone plate of the present invention may also have a portion of the shaft portion that is curved along the longitudinal axis. The portion of the shaft portion that is curved may preferably be in the form of an elliptical arc. In a preferred embodiment, the elliptical arc may be defined by a portion of an ellipse having a major axis with a length in the range of between about 150 mm and about 170 mm. Alternatively, the length of the major axis may be in the range from about 157 mm to about 163 mm. The elliptical arc may be further and/or alternatively defined by a portion of an ellipse having a minor axis with a length in the range of between about 60 mm and about 80 mm. Again alternatively, the length of the minor axis may range of between about 67 mm and about 73 mm.

According to the present invention, the bone plate may include a distal end of the shaft portion which lays in a first plane, and the head portion may lay in a second plane that is substantially parallel to the first plane. In yet another preferred embodiment, at least a portion of the bone plate may have a curvature that runs transversely to the longitudinal axis. The curvature may have a radius of curvature in the range from about 18 mm to about 22 mm. Preferably, the curvature may run substantially over the entire length of the bone plate.

The bone plate according to the present invention may further comprise an upper surface and a lower surface, wherein the longitudinal axis generally divides at least one of the upper and lower surfaces in half. In addition, at least a first pair of the first holes may be symmetrically disposed about the longitudinal axis and at least a second pair of first holes may be asymmetrically disposed about the longitudinal axis. The head portion may be connected to the shaft portion at a transition portion, and the at least one first pair of first holes may be located farther from the transition portion than is the at least one second pair of the first holes. In addition, at least one of the at least one second holes may define a central axis that is substantially perpendicular to the bone plate.

According to another embodiment of the bone plate according to the present invention, the bone plate comprises an elongated shaft portion and a widened head portion, the shaft portion and the head portion defining a common longitudinal axis extending substantially centrally along the bone plate. A first pair of screw holes may be located in the head portion, and the first pair of holes may include a first hole having a first central axis and a second hole having a second central axis, wherein the first and second holes are asymmetrically disposed about the longitudinal axis. A second pair of screw holes may be located in the head portion, and the second pair of holes may include a third hole having a third central axis and a fourth hole having a fourth central axis, wherein the third and fourth holes are symmetrically disposed about the longitudinal axis. The first central axis may lay in a first plane and the second central axis may lay in a second plane that is substantially parallel to the first plane. When the first central axis and the second central axis are projected onto a third plane substantially orthogonal to the longitudinal axis, the first central axis and the second central axis may intersect to form an acute angle. Preferably, the acute angle is between about 50° and about 60°. In yet another preferred embodiment, the acute angle may be between about 46° and about 54°.

According to the present invention, the third and fourth central axes may be substantially parallel to one another. Moreover, the bone plate may include an upper surface and a lower surface, wherein preferably, at least one of the third and fourth central axis forms an obtuse angle with respect to the lower surface. The obtuse angle may preferably range from about 92° to about 98°. In an alternative embodiment, the obtuse angle may range from about 94° to about 96°.

BRIEF DESCRIPTION OF THE DRAWINGS

Preferred features of the present invention are disclosed in the accompanying drawings, wherein similar reference characters denote similar elements throughout the several views, and wherein:

FIG. 1 is a top view of an illustrative embodiment of a bone plate according to the invention;

FIG. 2 is a sectional view of the bone plate of FIG. 1, taken along the line II-II of FIG. 1;

DETAILED DESCRIPTION OF THE PREFERRED EMBODIMENTS

Referring to FIGS. 1 to 4, an illustrative embodiment of a bone plate according to the present invention is shown. Bone plate P may be used for fixation of the long bones, such as, for example, fixation of the proximal humerus. Plate P may include an elongated shaft 1 having a length greater than its width x. Plate P may also have a head 2, preferably spoon-shaped, with a width y which is greater than the width x of the elongated shaft 1. The elongated shaft 1 and the head 2 may have a common longitudinal axis 3 and may be interconnected by a transition area 26. Transition area 26 may widen from the width x of the elongated shaft 1 to the width y of the head 2. According to one preferred embodiment, transition area 26 may widen exponentially from width x to width y.

Figure 5:
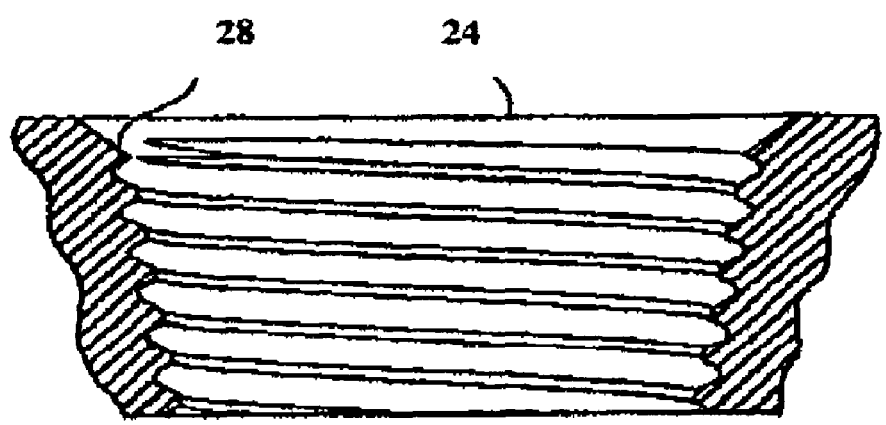
FIG. 5 is a partial sectional view of the bone plate of FIG. 1 taken along line V-V.

A large number of screw holes 9, 10. 16, 17, and 24 may be located in the elongated shaft 1 and in the head 2. In one preferred embodiment, the screw holes 24 provided in the elongated shaft 1 may have an inside thread 28 intended to engage a head of a bone screw. By using screws with a threaded bead, an angularly stable bone construct is formed which can maintain the hold of the bone plate even under dynamic conditions. Preferably, the inside thread may be multithreaded. for example, double-threaded, as shown in FIG. 5. In an alternative embodiment, holes 24 may include one or more partially peripheral wedge-shaped grooves or keys intended to engage a head of a bone screw. The central axes of the holes 24 in the elongated shaft may be substantially perpendicular to the upper and/or lower surfaces of the shaft 1.

The screw holes 9, 10, 16, 17, located in the head 2 of the bone plate P may also have an inside thread 27 for engaging a head of a bone screw. Thread 27 is preferably multithreaded, for example, double-threaded (similar to the configuration discussed above with reference to FIG. 5). The inside thread 27 may alternatively have partially peripheral wedge-shaped grooves or keys for engaging the head of a bone screw.

The thread pitch of inside threads 27, 28 or the partially peripheral wedge-shaped groove or key is preferably about 0.8 mm, although other pitches are possible. This relatively small thread pitch may allow secure anchoring of the screw head in a thin section of the plate P. For example, a section having a thickness in the range from about 1 mm to about 2 mm. Accordingly, the thickness of the plate may be made very thin without adversely affecting the stability of the plate-screw construct. The thickness of the bone plate preferably is about 2 mm.

Figure 4:
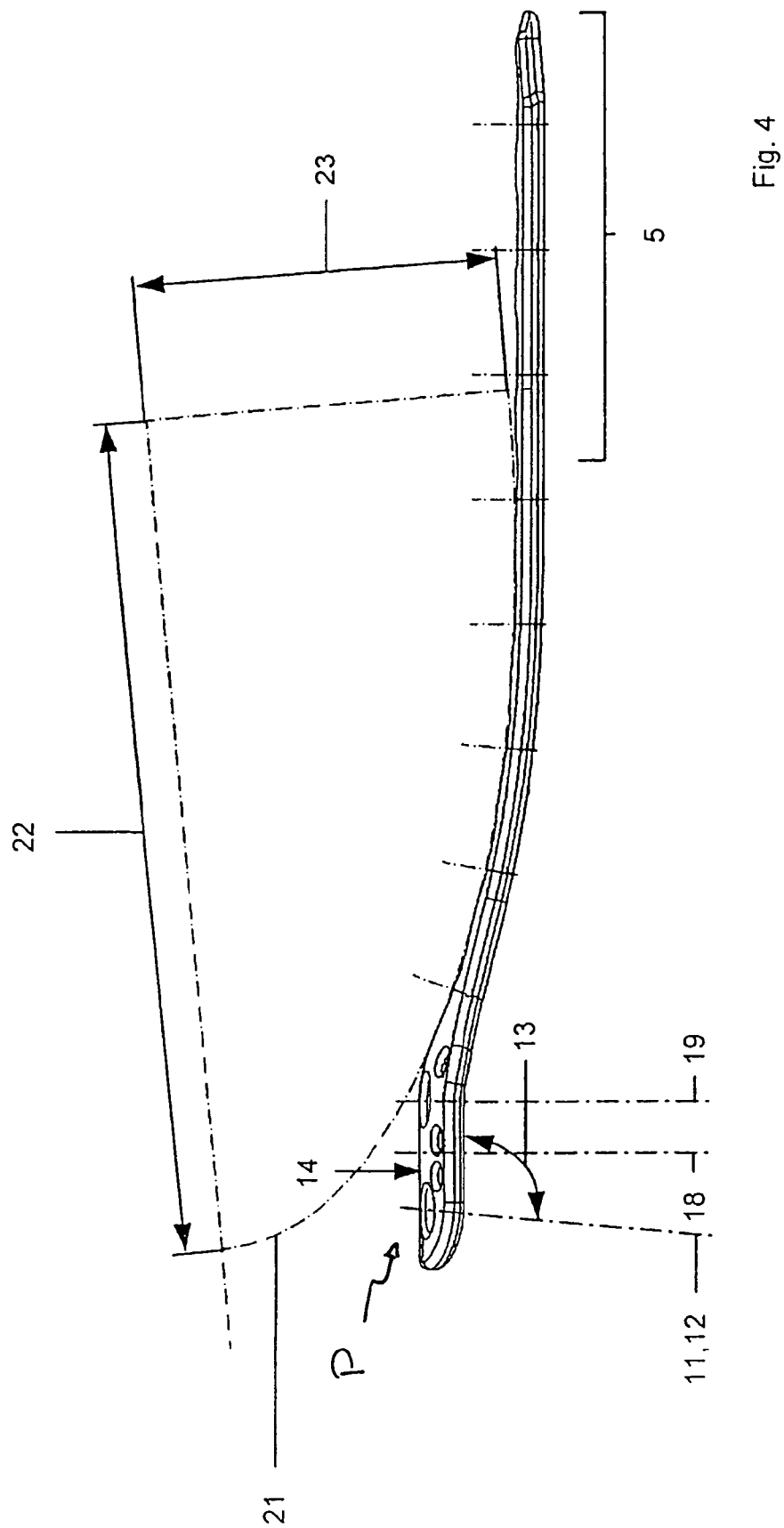
FIG. 4 is a side view of the bone plate of FIG. 1.

As shown in FIG. 4, the elongated shaft 1 may be shaped and dimensioned to match the anatomy of the unbroken human proximal humerus. For example, shaft 1 when viewed in the direction of the central axis 3, may be at least partially curved. The curvature may be defined by an elliptical arc 21, in which case, the length of the major axis 22 of the ellipse which defines the elliptical arc 21 may be in the range of between about 150 mm and about 170 mm. More preferably, the length of the major axis may be in the range from about 157 mm to about 163 mm. According to one preferred embodiment, the length of the major axis 22 may be about 160 mm. The length of the minor axis 23 of the ellipse which defines the elliptical arc 21 may be in the range of between about 60 mm and about 80 mm. More preferably, the length of the minor axis 23 may be in the range of between about 67 mm and about 73 mm. According to one preferred embodiment the length of the minor axis 23 may be about 70 mm. The curvature of the elongated shaft I and/or the head 2 may be configured and dimensioned such that the free end 5 of the elongated shaft 1 and the head 2 lay in planes which are substantially parallel to one another. By providing plate P with the above-described shape and configuration, the plate P may rest cleanly on the bone without interfering with any of the relevant anatomic structures.

At least a portion of bone plate P may have a curvature which runs transversely to the central axis 3. Preferably, the curvature has a radius of curvature in the range of about 18 mm to about 22 mm. As shown in the exemplary embodiment of FIG. 2, the bone plate P may have a curvature 6 (transverse to the central axis 3) with a radius of curvature of about 20 mm. The curvature may extend substantially over the entire length of plate P. One advantage of the bone plate configuration is that no irritation of the soft tissue occurs. For example, when the arm is raised, the bone plate is prevented from hitting the acromion of the shoulder.

As shown in FIGS. 1 and 2, the proximal portion 8 of the head 2 (i.e., the free end) may have at least two holes 9, 10 which are arranged substantially symmetrically to the central axis 3. Referencing FIG. 4, holes 9, 10 may have axes 11, 12, which may form an angle 13 with the surface 14. The angle 13 may range from about 92° to about 98°, and preferably from about 94° to about 96°. According to one preferred embodiment, angle 13 may be about 95°. By using screws with a threaded head, an angularly stable bone construct may be formed which can maintain the hold of the bone plate even under dynamic conditions. A contact angle in these ranges may increase the contact surface with the solid bone since solid bone material may be present only in the edge zones of the relatively hollow humerus head.

Figure 3:
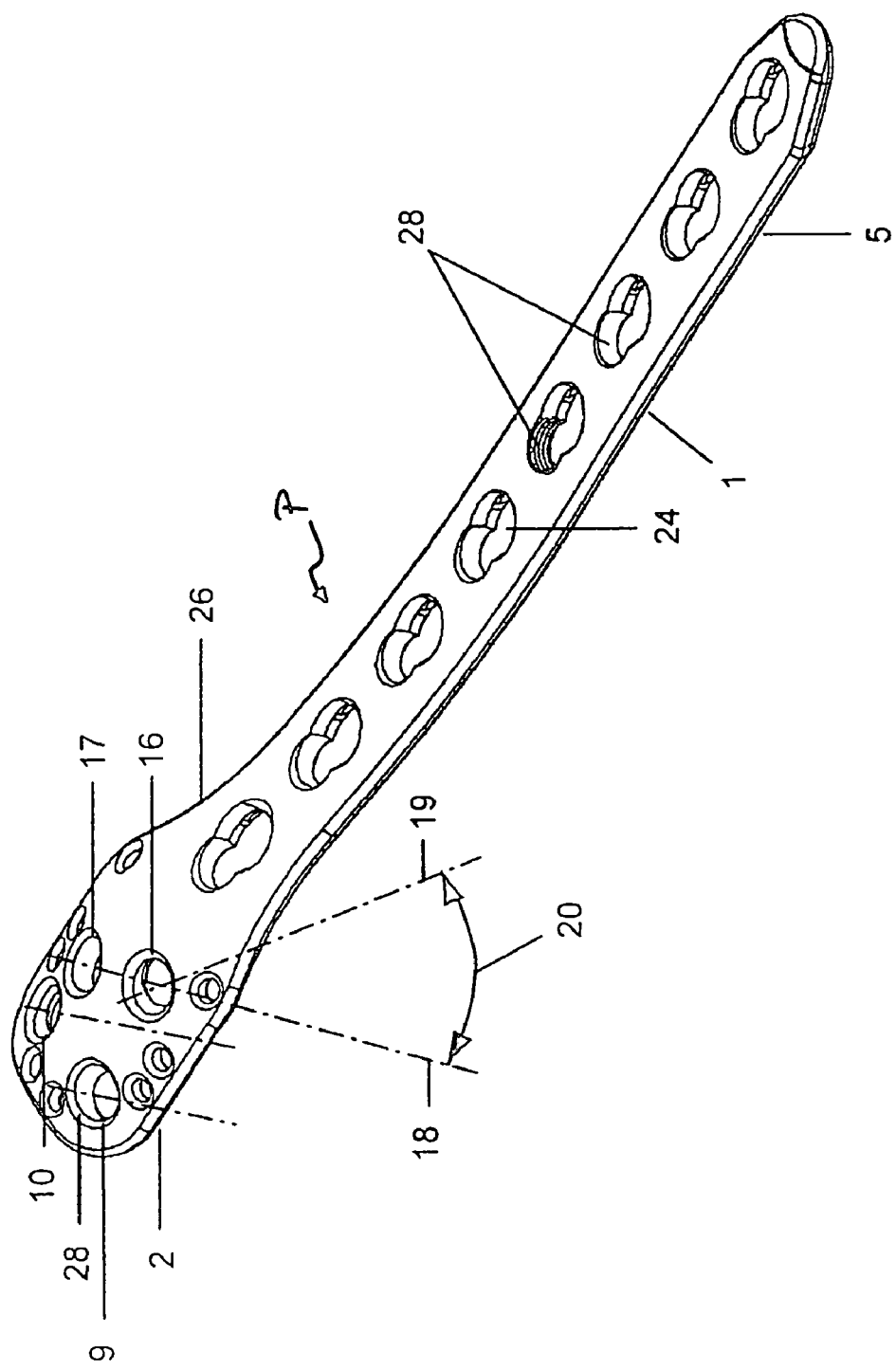
FIG. 3 is a perspective view of the bone plate of FIG. 1.

As shown in FIGS. 1 and 3, the distal portion 15 of the head 2 (which may border the transition area 26, if provided) may have two holes 16, 17 which may be arranged asymmetrically to the central axis 3. Holes 16, 17 may have axes 18, 19 which may lay in planes that are parallel to one another and/or which may be orthogonal to the central axis 3. The projection of axis 18 into the parallel plane which contains axis 19 may include an angle 20. Angle 20 may be preferably in the range of about 40° to about 60°, more preferably about 46° to about 54°. According to one preferred embodiment, angle 20 may be about 50°. One advantage of this configuration is that one or more of the screws which are to be inserted into holes 16, 17 may be anchored in the small tuberculum, which often breaks in fractures of the proximal humerus. It may be more preferable that none of the axes 11, 12, 18, 19 of holes 9, 10, 16, 17 (which may be arranged symmetrically and/or asymmetrically to the central axis 3) intersect. According to this configuration, the bone screws which are to be inserted into the holes 9, 10, 16, 17 do not interfere with one another.

While preferred embodiments and features of the present invention have been disclosed herein, it will be appreciated that numerous modifications and embodiments may be devised by those skilled in the art. It is intended that the appended claims cover all such modifications and embodiments as fall within the scope of such claims and that the claims not be limited to or by such preferred embodiments or features.

What is claimed:

1. A bone plate for fixation of a fractured bone, the bone plate comprising:
   an elongated shaft portion and a widened head portion, the shaft portion and the head portion defining a common longitudinal axis extending substantially centrally along the bone plate;
   a first pair of screw holes located in the head portion, the first pair of holes include a first hole having a first central axis and a second hole having a second central axis, wherein the first and second holes are asymmetrically disposed about the longitudinal axis;
   a second pair of screw holes located in the head portion, the second pair of holes include a third hole having a third central axis and a fourth hole having a fourth central axis, wherein the third and fourth holes are symmetrically disposed about the longitudinal axis;
      wherein the first central axis lies in a first plane and the second central axis lies in a second plane that is substantially parallel to the first plane, further wherein when the first central axis and the second central axis are projected onto a third plane substantially orthogonal to the longitudinal axis, the first central axis and the second central axis intersect to form an acute angle.

2. The bone plate of claim 1, wherein the acute angle is between about 40° and about 60°.

3. The bone plate of claim 2, wherein the acute angle is between about 46° and about 54°.

4. The bone plate of claim 1, wherein the third and fourth central axes are substantially parallel to one another.

5. The bone plate of claim 1, wherein the bone plate includes an upper surface and a lower surface, and at least one of the third and fourth central axis forms an obtuse angle with respect to the lower surface.

6. The bone plate of claim 5, wherein the obtuse angle ranges between about 92° and about 98°.

7. The bone plate of claim 6, wherein the obtuse angle ranges between about 94° and about 96°.

8. The bone plate of claim 1, wherein at least one of the first, second, third and fourth screw holes includes a threading to engage a head of a bone screw.

9. The bone plate of claim 8, wherein the threading has a pitch of between about 0.5 mm and about 1.1 mm.

10. The bone plate of claim 8, wherein the threading is a double thread.

11. The bone plate of claim 1, wherein the bone plate has a thickness ranging from about 1.7 mm to about 2.3 mm.

12. The bone plate of claim 1, wherein at least a portion of the shaft portion is curved along the longitudinal axis in the form of an elliptical arc.

13. The bone plate of claim 12, wherein the elliptical arc is defined by a portion of an ellipse having a major axis with a length in the range of between about 150 mm and about 170 mm and a minor axis with a length in the range of between about 60 mm and about 80 mm.

14. The bone plate of claim 1, wherein at least a portion of the bone plate has a curvature that runs transversely to the longitudinal axis, the curvature having a radius of curvature in the range from about 18 mm to about 22 mm.

15. The bone plate of claim 1, wherein the head portion and the shaft portion are shaped and dimensioned to substantially match a proximal humerus.

16. A bone plate for fixation of proximal humerus fractures comprising:
   an upper surface;
   a lower surface;
   an elongated shaft portion having a first width;
   a head portion connected to the shaft portion and having a second width greater than the first width, the head portion and the shaft portion defining a common longitudinal axis, the longitudinal axis generally dividing at least one of the upper and lower surfaces in half;
   at least one first screw hole located in the head portion;
   at least one second screw hole located in the shaft portion;
      wherein at least one of the first and second screw holes is at least partially threaded to engage a head of a bone screw to form an angularly stable connection with the bone screw, and further wherein at least a first pair of the first screw holes is symmetrically disposed about the longitudinal axis, and at least a second pair of the first screw holes is asymmetrically disposed about the longitudinal axis.

17. The bone plate of claim 16, wherein the at least one first screw hole in the head portion is configured differently than the at least one second screw hole in the shaft portion.

18. The bone plate of claim 17, wherein the at least one second screw hole is elongated along the longitudinal axis of the plane.

* * * * *

UNITED STATES PATENT AND TRADEMARK OFFICE
CERTIFICATE OF CORRECTION

PATENT NO. : 7,655,029 B2
APPLICATION NO. : 10/721895
DATED : February 2, 2010
INVENTOR(S) : Niederberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1375 days.

Signed and Sealed this

Twenty-third Day of November, 2010

David J. Kappos
*Director of the United States Patent and Trademark Office*